(12) United States Patent
Forrester et al.

(10) Patent No.: US 9,750,553 B1
(45) Date of Patent: Sep. 5, 2017

(54) INTERPHALANGEAL FUSION IMPLANT (71) Applicants: Perry Forrester, Houston, TX (US); Joshua Scott, Houston, TX (US)

(72) Inventors: Perry Forrester, Houston, TX (US); Joshua Scott, Houston, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 527 days.

(21) Appl. No.: 13/758,617

(22) Filed: Feb. 4, 2013

Related U.S. Application Data

(60) Provisional application No. 61/594,154, filed on Feb. 2, 2012.

(51) Int. Cl.
  *A61B 17/86* (2006.01)
  *A61B 17/84* (2006.01)

(52) U.S. Cl.
  CPC .......... *A61B 17/8605* (2013.01); *A61B 17/84* (2013.01); *A61B 17/864* (2013.01)

(58) Field of Classification Search
  CPC .... A61F 2/4604; A61F 2/4225; A61F 2/4241; A61F 2002/4228; A61F 2002/4243; A61F 2002/4246; A61F 2002/4248; A61B 17/864; A61B 17/7291
  USPC .............................. 606/304; 623/21.19, 21.15
  See application file for complete search history.

(56) References Cited

U.S. PATENT DOCUMENTS

| 2,172,355 | A | * | 9/1939 | Brady | 84/459 |
|---|---|---|---|---|---|
| 2010/0329817 | A1 | * | 12/2010 | Connors | F16B 15/02 411/389 |
| 2011/0004255 | A1 | * | 1/2011 | Weiner | A61B 17/1682 606/301 |
| 2011/0301652 | A1 | * | 12/2011 | Reed et al. | 606/319 |
| 2012/0089197 | A1 | * | 4/2012 | Anderson | A61B 17/7233 606/310 |
| 2013/0066383 | A1 | * | 3/2013 | Anderson et al. | 606/329 |
| 2013/0131822 | A1 | * | 5/2013 | Lewis et al. | 623/21.19 |

* cited by examiner

*Primary Examiner* — David Bates
*Assistant Examiner* — Olivia C Chang
(74) *Attorney, Agent, or Firm* — Bushman Werner, P.C.

(57) ABSTRACT

An interphalangeal fusion implant comprising a threaded shank and a head, the head having a body portion having first and second laterally spaced fins, each of which has a plurality of axially spaced serrations, some of the serrations terminating at the laterally outermost ends at substantial single points. A driver for implanting an interphalangeal fusion implant comprising an elongate body, a receiving formation having at least two radially extending outward projections, and a pear shaped portion extending along a central axis of the body. A method of fusing a first phalanx and a second phalanx using an interphalangeal fusion implant.

22 Claims, 10 Drawing Sheets

INTERPHALANGEAL FUSION IMPLANT

CROSS REFERENCE TO RELATED APPLICATION

This application claims priority to U.S. Application No. 61/594,154 filed on Feb. 2, 2012, the disclosure of which is incorporated herein by reference for all purposes.

FIELD OF THE INVENTION

The present invention relates to bone implants or pins, and more particularly to an interphalangeal fusion implant which provides an anatomically correct angle between a first phalanx and a second, adjacent phalanx, e.g., the proximal phalanx and the intermediate phalanx which exists at the proximal interphalangeal joint.

BACKGROUND OF THE INVENTION

Digital deformities of the fingers and toes are some of the most common conditions encountered by orthopedists and podiatrists. Patients with digital deformities often experience significant pain from structural abnormalities. Some of these abnormalities are acquired, caused by traumatic injuries, neuromuscular pathologies, systemic diseases, mechanical problems secondary to extrinsic pressures, or intrinsic muscular imbalances. The deformities are popularly known as mallet finger, jersey finger, coach's finger, hammer toe, mallet toe, claw toe, as well as a host of others indicative of several different pathologies.

Hammer toe is generally described in the medical literature as an acquired disorder, typically characterized by hyperextension of the metatarsophalangeal joint (MTPJ), hyperflexion of the proximal interphalangeal joint (PIPJ), and hyperextension of the distal interphalangeal joint (DIPJ). Although this condition can be conservatively managed (e.g., through the use of orthotic devices), in certain instances surgical intervention is required.

In order to prevent recurrence of the deformity and ensure the success of the surgical procedure, a proximal interphalangeal (PIP) joint arthrodesis is typically performed. The "end-to-end" or "peg-in-hole" techniques are the most commonly used procedures. The PIPJ is aligned with the rest of the toe in a corrected anatomical position and maintained in place by the use of a 0.045 Kirschner wire (K-wire) which is driven across the joint. Initially, the wire is placed from the PIPJ through the tip of the toe. It is then driven in retrograde fashion into the proximal phalanx. The exposed wire exiting the toe is bent to an angle greater than 90 degrees, and the bent portion is cut at 1 cm from the bend. At the conclusion of the surgical procedure, a small compressive dressing is placed around the forefoot to stabilize the toe, and the foot is immobilized with or without a rigid splint. The K-wire and the splinting are generally removed six weeks after surgery. Similar procedures may be followed to create arthrodesis of the distal interphalangeal joint (DIP) of the toe or for arthrodesis performed in the finger to correct digital abnormalities of the hand.

SUMMARY OF THE INVENTION

In one aspect, the present invention provides an interphalangeal fusion implant for use in effecting interphalangeal fusion between a first phalanx and a second, adjacent phalanx.

In another aspect, the present invention provides an interphalangeal implant for the correction of hammer toe.

In yet another aspect, the present invention provides a cannulated intramedullary fusion system which can have a variety of configurations to match patient anatomy and achieve the desired results.

In still a further aspect, the present invention provides a method for joining a first phalanx to a second, adjacent phalanx.

In another aspect, the present invention provides a driver for use in driving an interphalangeal fusion implant into the bone.

These and further features and advantages of the present invention will become apparent from the following detailed description, wherein reference is made to the figures in the accompanying drawings.

DETAILED DESCRIPTION OF PREFERRED EMBODIMENTS

While the invention will be described with particular reference to the correction of hammer toe, it will be understood that it is not so limited. The implant and method of the present invention can be used to correct other digital deformities.

Referring first to FIGS. 10-13, there is shown one embodiment of the implant of present invention. The implant shown generally as 10 comprises a threaded shank 12 and a head shown generally as 14. Head 14 comprises a body portion 16 proximal said shank 12 and a nose portion 18 distal said shank 12. As can be seen, nose 18 is generally wedge shaped. Body portion 16 has a first side or fin 20 and a second side or fin 22, sides 20 and 22 being laterally spaced. Body portion 16 has a first facet 24, a second facet 26, a third facet 28, and a fourth facet 30. Facets 24 and 26 form a first or top surface of body portion 16, while facets 28 and 30 form a second or bottom surface of body portion 16. As can be seen with particular reference to FIGS. 10 and 12, facets 24 and 26 extend downwardly and outwardly from the centerline 32 of the top surface of body portion 16 while facets 28 and 30 extend upwardly and outwardly from the centerline 34 of the bottom of surface of body portion 16. Accordingly, body portion 16 is generally diamond-shaped when viewed in transverse cross-section, as thus seen in FIG. 12.

Figure 11:
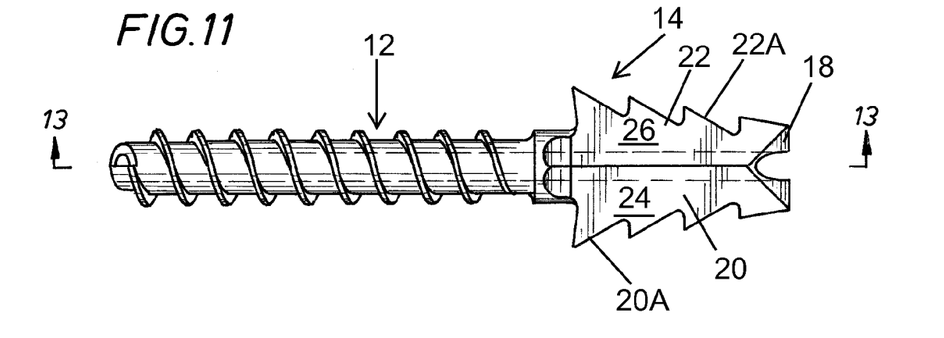
FIG. 11 is a side, elevational view of the implant of FIG. 10.
Figure 12:
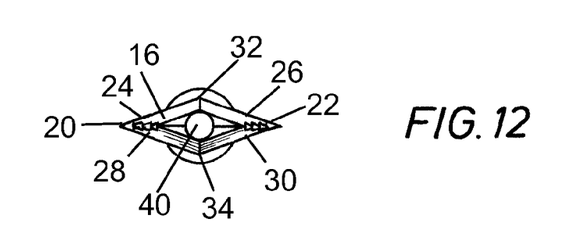
FIG. 12 is an end view of the implant of FIG. 10.
Figure 13:
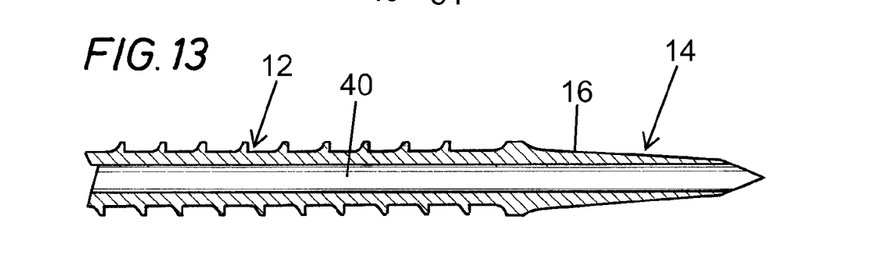
FIG. 13 is a cross-sectional view taken along the line 13-13 of FIG. 11.

As can be seen with reference to FIG. 11, sides 20 and 22 taper in a converging manner from a location proximal shank 12 to nose 18. Furthermore, sides 20 and 22 each have a series of serrations or barbs indicated as 20A on side 20 and 22A on side 22. As can also be seen with reference to FIGS. 10 and 11, because of the converging nature of the surfaces formed by facets 24, 26, 28, and 30 and the serrations 20A and 22A, the laterally outermost ends of the serrations terminate at substantial single points, indicated at 20B with respect to serration 20A, and 22B with respect to serration 22A. Although not absolutely necessary, the serrations proximal shank 12 have an included angle of slightly less than 90°, e.g. at an angle of from about 20° to about 90° as measured relative to the long axis passing through shank 12. The undercut angle of the serration proximal shank 12 allows greater gripping of tissue when the implant is fully positioned in the phalanx.

An important feature of the implant of the present invention is the provision of a cannula 40 which in a preferred case is substantially straight and which extends through shank 12 and head 14.

Referring now to FIGS. 14-17, there is shown another embodiment of the implant of the present invention. Implant 50 comprises a shank 52 and a head 54, head 54 comprising a body portion 56 and a generally wedge shaped nose portion 58. The implant shown generally as 50 differs from implant 10 in that the head 54 of implant 50 is angled relative to a long axis passing through the shank 52.

Figure 14:
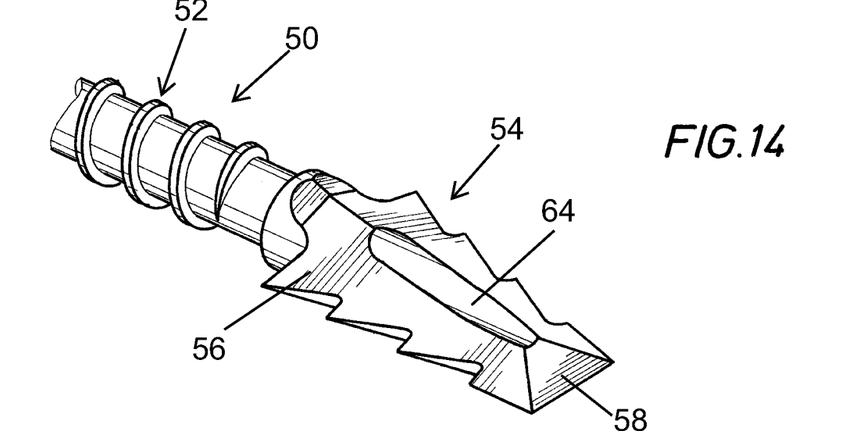
FIG. 14 is an isometric view of another embodiment of the implant of the present invention.
Figure 15:
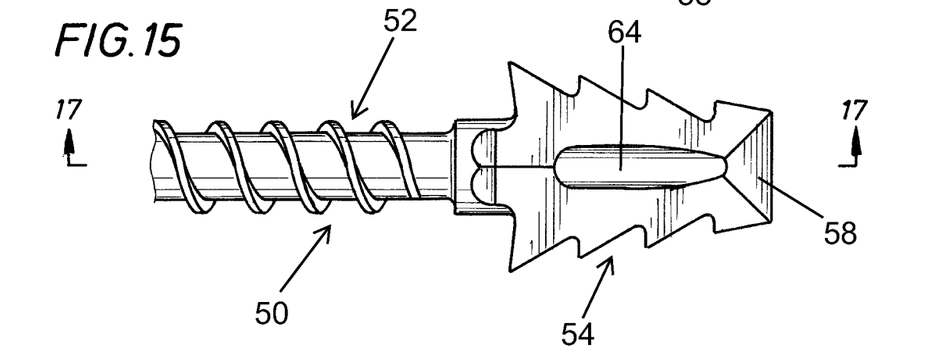
FIG. 15 is a side, elevational view of the implant shown in FIG. 14.
Figure 16:
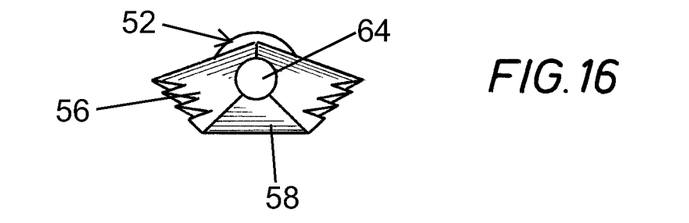
FIG. 16 is an end view of the implant shown in FIG. 14.
Figure 17:
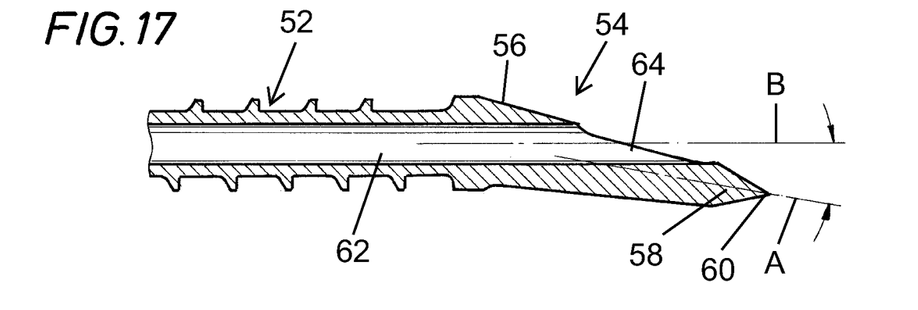
FIG. 17 is a cross-sectional view taken along the line 17-17 of FIG. 15.

In this regard, as seen in FIG. 17, an axis A passing generally through the centerline of head 54 and the tip 60 of nose portion 58 is at an angle to the long axis B passing through shank 52. The angle is about 10° but can be varied as desired to accommodate various anatomical scenarios. In most other respects, implant 50 is quite similar to implant 10 in that head 54 is generally diamond-shaped when viewed in transverse cross-section, head 54 is tapered and has serrated edges, the outermost ends of the serrations terminating at substantial single points. Thus, other than the angular relationship between the head 54 and the shank 52, the implant 50 shown in FIGS. 14 and 17 is substantially the same as implant 10, with the proviso that since the cannula 62 is substantially straight, it forms a channel of decreasing depth along head 54. It will be understood that the depth of the channel will vary as the angle between axis A and axis B shown in FIG. 17 varies. Further, head 54 may be attached to shank 52 as to be offset such that cannula 62 does not pass through any portion of head 54.

Head 54 being at an angle to an axis passing through shank 52 provides an advantage in the healing of the toe. In a normal toe, the proximal phalanx and intermediate phalanx are not in straight alignment with one another, but rather they rest at a slight angle to one another. The angle of head 54 in this embodiment corresponds to the resting angle of the toe and thus provides improved healing and shaping of the toe. As previously noted, the angle can be varied to best accommodate the toe of the patient. This embodiment has a further advantage in that it also includes a cannula. Thus, the K-wire method described below and shown in FIGS. 1-6, can be performed using the angled implant shown in FIGS. 14-17. While in the embodiments described above, the head 14, 54 of the implant of the present invention is generally diamond-shaped when viewed in transverse cross-section, it is to be understood that the shape is not so limited. Thus, the head could have any number of generally oblong cross-sectional configurations, such as ellipsoidal, elliptical, elongate, ovaliform, ovaloid, ovate, ovated, ovoid, etc., or any number of generally non-oblong cross-sectional configurations.

While the embodiments shown in FIGS. 10-17 show two sides or fins on the head portion, it will be understood that the head could include any number of laterally outward projections. Additionally, as shown, there are a plurality of serrations, it will be understood that the implant of the present invention can be made with a single serration.

Figure 1:
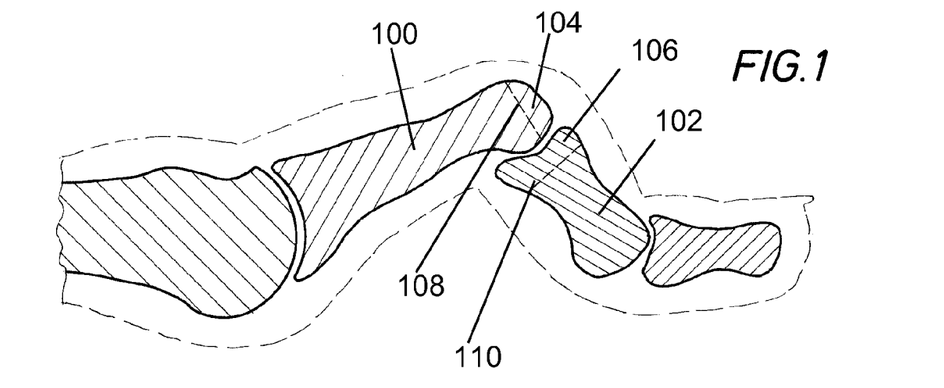
FIG. 1 is a cross-sectional view of a portion of a human foot showing a hammer toe condition.

Referring now to FIGS. 1-6, there is shown one method of performing a proximal interphalangeal joint orthodesis, in this case being exemplified by a deformity known as hammer toe. FIG. 1 shows a cross-sectional view of a typical hammer toe condition. As can be seen, there is a marked angular displacement between the proximal phalanx 100 and the intermediate phalanx 102. To correct this condition, and in accordance with one aspect of the present invention, the distal portion 104 of the proximal phalanx 100 and the proximal portion 106 of the intermediate phalanx 102 are resected as indicated by the dotted lines 108 and 110, respectively.

Figure 2:
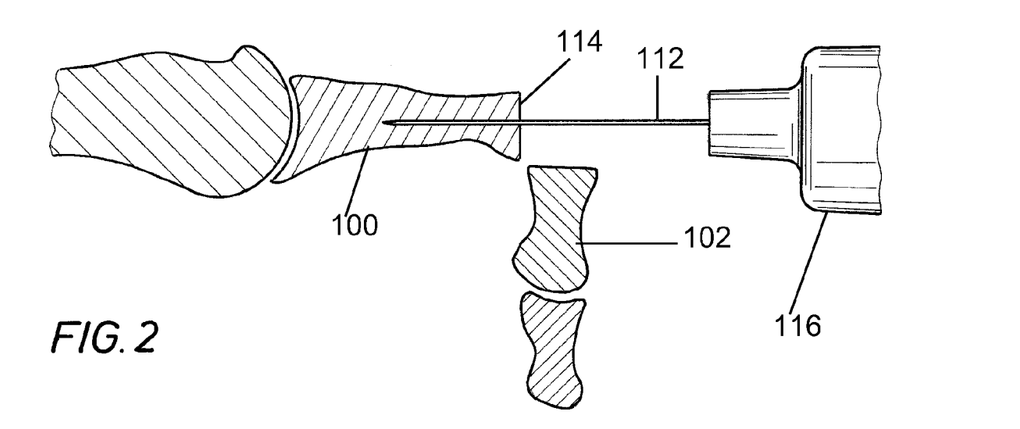
FIG. 2 is a partial cross-sectional view of the hammer toe shown in FIG. 1 which has had portions of the proximal and middle or intermediate phalanges resected and the placement of a K-wire into the resected surface of the proximal phalanx.
Figure 3:
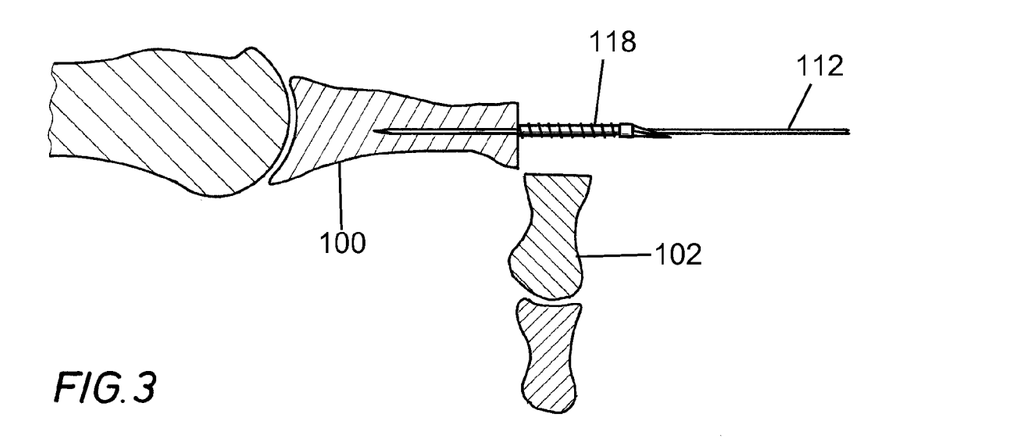
FIG. 3 is a view similar to FIG. 2 but showing the implant of the present invention placed over the K-wire in sliding relationship prior to be driven into the proximal phalanx.

Turning to FIG. 2 a K-wire 112 is introduced through the resected surface 114 of the proximal phalanx using a suitable driver 116. Following this, an appropriate sized implant according to the present invention, indicated at 118 in FIG. 3 is slid over the K-wire 112, the K-wire 112 extending through the cannula of the implant.

Figures 4, 5:
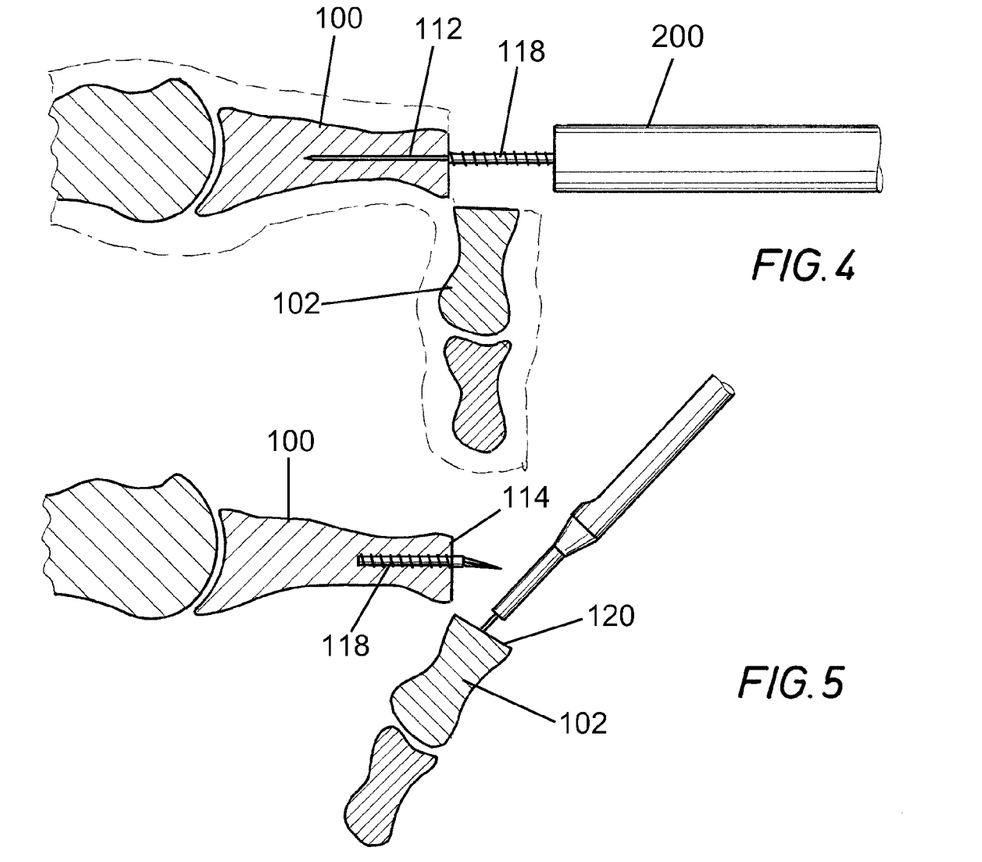
FIG. 4 is a view similar to FIG. 3 but showing a driver in position to drive the implant of the present invention into the proximal phalanx.
FIG. 5 is a cross-sectional view of the resected phalanges with a portion of the implant of the present invention received in the proximal phalanx and a hole being drilled into the resected surface of the intermediate phalanx prior to being broached for receipt of the free end of the implant.
Figure 6:
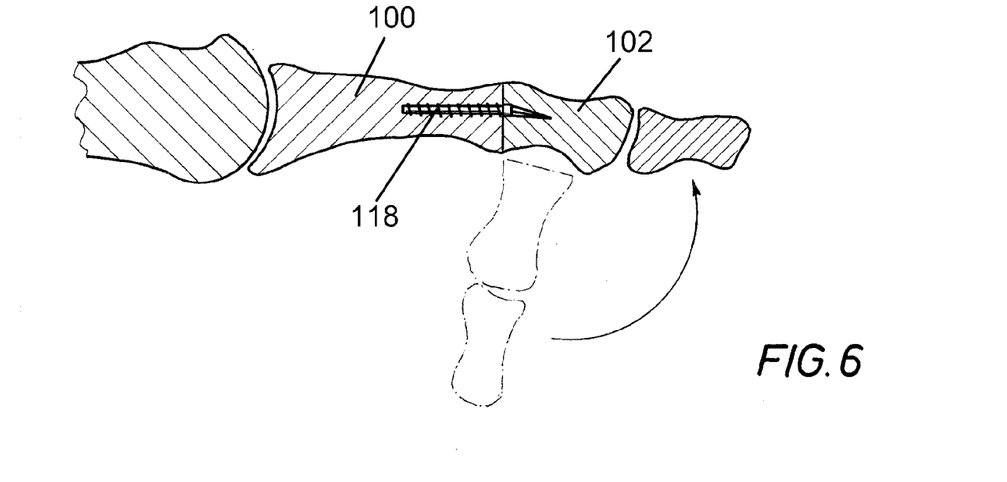
FIG. 6 is a view showing repositioning of the middle phalanx relative to the proximal phalanx whereby the free end of the implant protruding from the proximal phalanx is received in the broached hole in the middle phalanx.

Referring now to FIG. 4, a driver 200 engages the head of the implant 118 and threads it into the resected surface 114 of the proximal phalanx 100. As can be seen in FIG. 5, when this is done most of the threaded shank portion of the implant 118 is received in the proximal phalanx 100 while the head portion of the implant 118 protrudes from the resected surface 114 thereof. At this point, and depending on the density of the bone, it may be desirable to drill a hole in resected surface 120 of the intermediate phalanx 102 at the point where a broached hole will be placed for receipt of the head of the implant 118. Once this is done, the broached hole in intermediate phalanx 102 is placed over the head 118 and pressure is exerted on the intermediate phalanx until resected surfaces 114 and 120 are in substantial engagement, as shown in FIG. 6.

Figures 7, 8, 9:
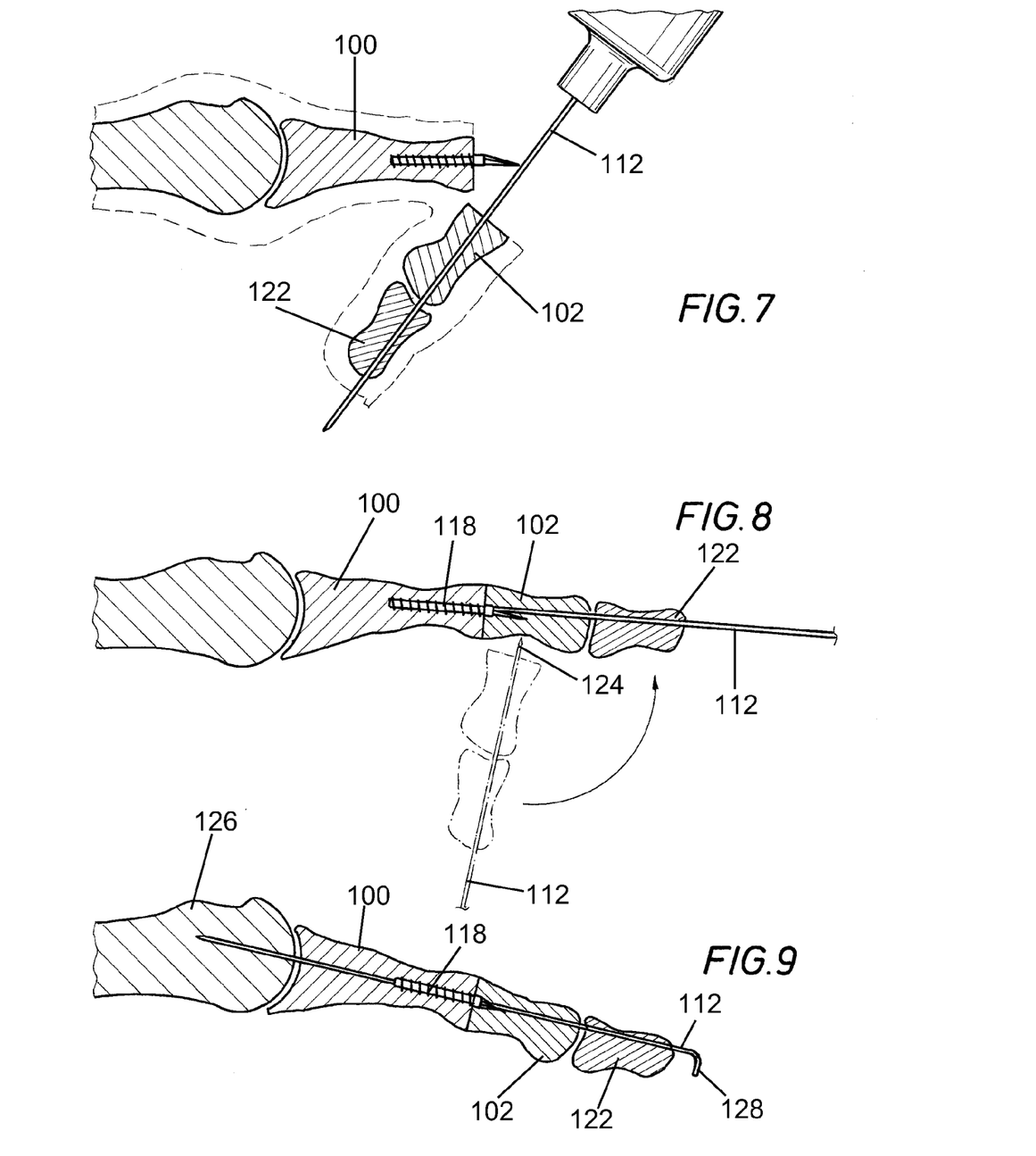
FIG. 7 is a view similar to FIG. 5 but showing a K-wire extending through the middle phalanx and the distal phalanx.
FIG. 8 is a view similar to FIG. 6 showing repositioning of the intermediate phalanx whereby the free end of the implant is received in the broached hole in the intermediate phalanx with the K-wire extending out of the end of the distal phalanx.
FIG. 9 is a view similar to FIG. 6 showing repositioning the proximal and intermediate phalanx and a K-wire extending into the metatarsal, through the proximal, intermediate and distal phalanges and protruding from the end of the latter.
Figure 10:
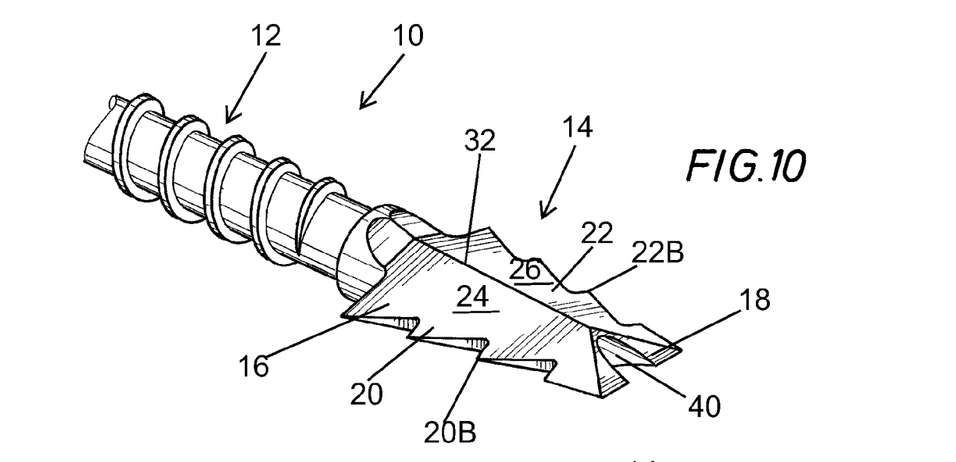
FIG. 10 is an isometric view showing one embodiment of the implant of the present invention.

Referring now to FIGS. 7-9, there is shown another method of using the present invention. In connection with performing the method set forth in FIGS. 7-9, it will be understood that the steps shown in FIGS. 1-5 will have already been performed. The method set forth in FIGS. 7-9 differ from that shown in FIGS. 1-6 in that, as can be seen in FIG. 7, a K-wire is driven through the intermediate phalanx 102 as well as out the tip of the distal phalanx 122. Next, as shown in FIG. 8, the intermediate phalanx 102 and proximal phalanx 100 are engaged with the head of the implant 118 received in the broached hole of the intermediate phalanx 102. As can be seen in FIG. 8, following repositioning of the intermediate phalanx 102 to abut the resected surface of the proximal phalanx 100, the pointed tip 124 of the K-wire 112 extends through the distal and intermediate phalanges 122, 102, respectively, and is received in the mouth of the cannula formed in the head of the implant 118. The K-wire 112 is then driven through the proximal phalanx 100 into the metatarsal 126 such that the K-wire 112 now extends from the metatarsal through the proximal, intermediate, and distal phalanges, a portion 128 of the K-wire 112 extending out of the tip of the proximal phalanx 122, a portion 128 being bent at an angle of 90° or greater.

Turning now to FIGS. 18-30, there is shown the driver used in connection with the implant of the present invention. It will be understood that while FIGS. 18-30 show an embodiment of the driver being used with the angled head implant shown in FIGS. 14-17, other driver embodiments could be used with the straight head implant shown in FIGS. 10-13. Further driver embodiments could be used with implants having heads of various configurations from those depicted in the figures.

Figure 18:
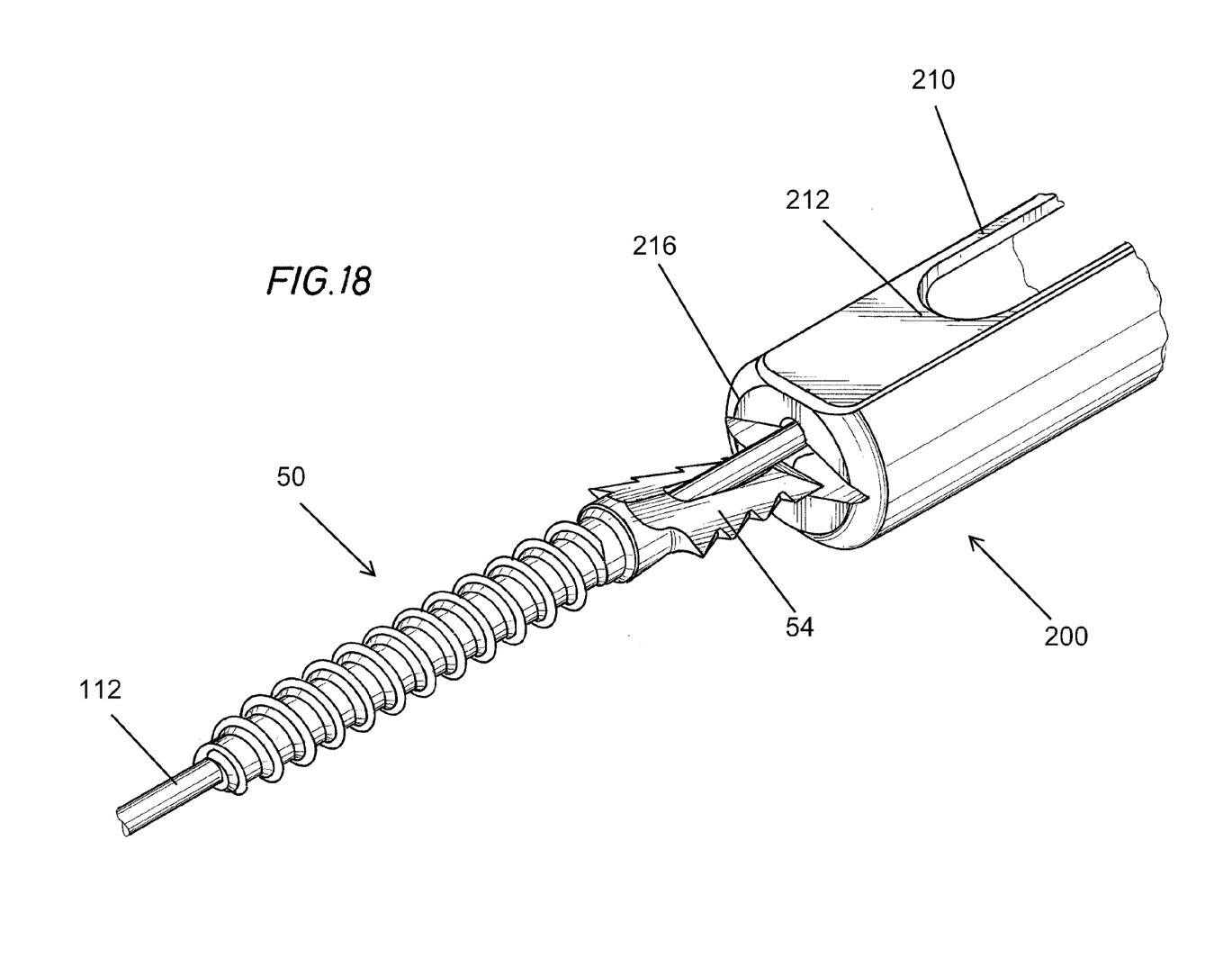
FIG. 18 is an isometric view showing the driver of the present invention showing the implant of the present invention before insertion into the driver.
Figure 19:
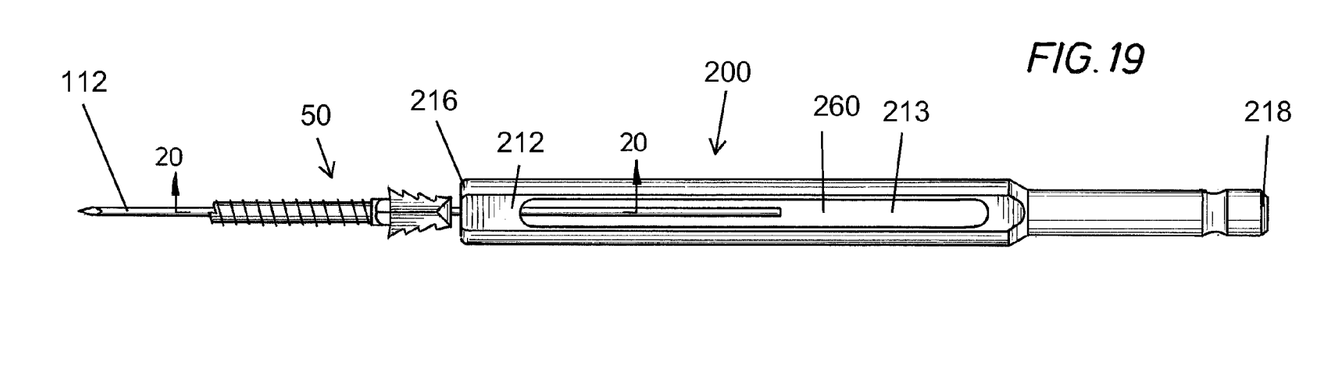
FIG. 19 is a top view of the driver of the present invention showing the implant of the present invention before insertion into the driver.
Figure 20:
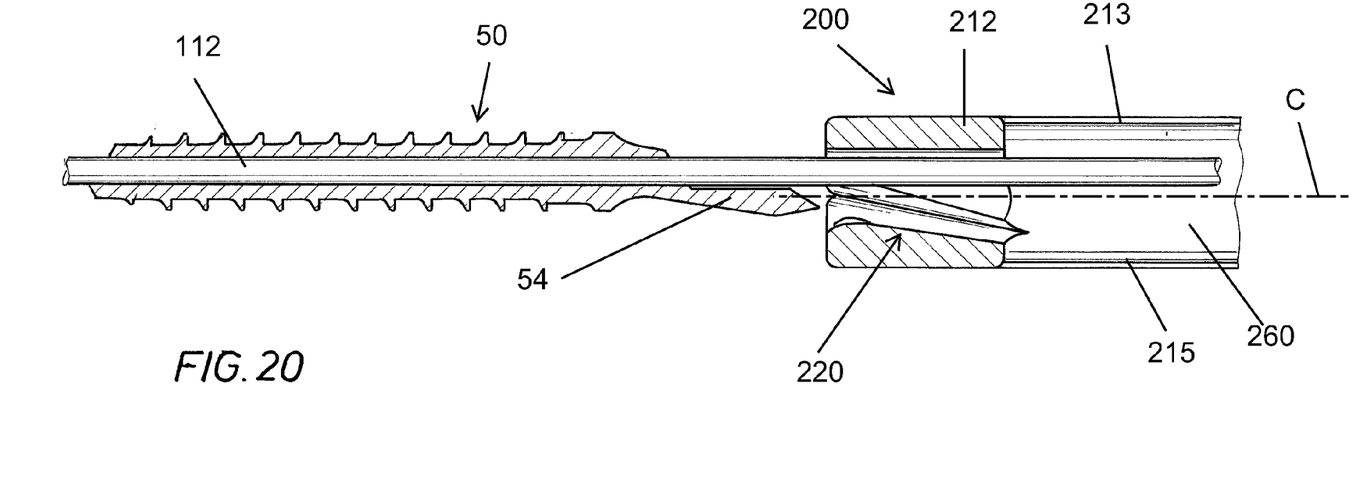
FIG. 20 is a cross-sectional view taken along the line 20-20 of FIG. 19.
Figure 21:
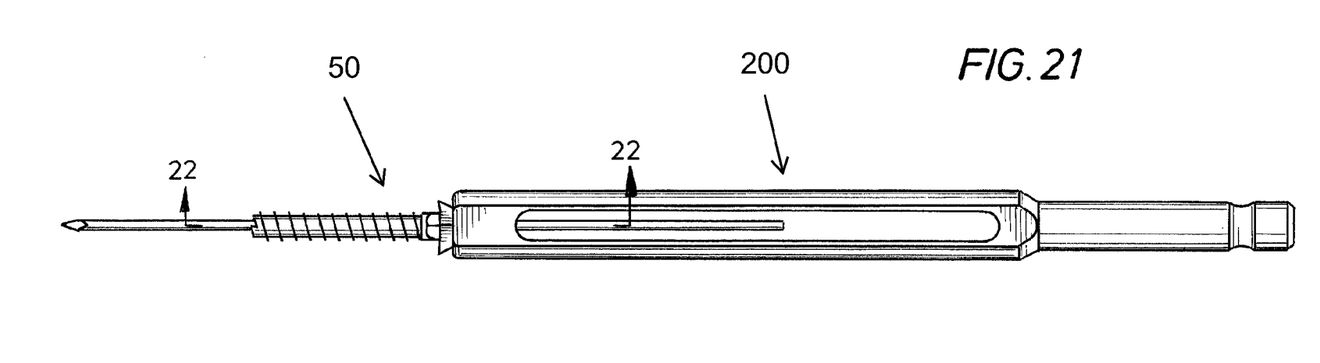
FIG. 21 is a top view of the driver of the present invention when the implant of the present invention is partially inserted into the driver.

FIGS. 18-24 depict a driver, shown generally as 200, as it is used in connection with K-wire 112 and implant 50 of the present invention. As best seen in FIGS. 18 and 19, driver 200 includes an elongate body 210, having a first end 216, and a second end 218. As best seen in FIG. 20, first end 216 of driver 200 is in open communication with a receiving formation shown generally as 220 and discussed more fully hereafter.

Figures 25, 26, 27:
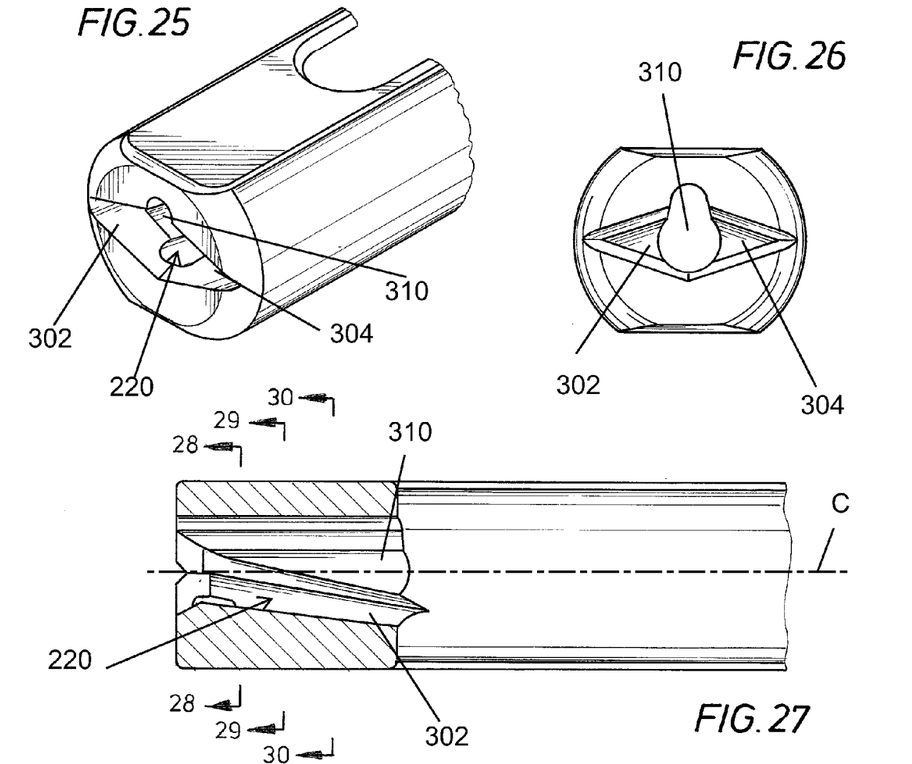
FIG. 25 is a partial isometric view of the driver of the present invention.
FIG. 26 is an end view of the driver shown in FIG. 18.
FIG. 27 is a cross-sectional view of a portion of the driver shown in FIG. 18.

Turning now to FIGS. 25-30, and with particular reference to FIG. 27, it can be seen that in general, receiving formation 220 extends longitudinally into body 210. As best seen in FIG. 26, at first end 216 of driver 200, receiving formation 220 is comprised of two radially outwardly extending portions 302 and 304 which are generally triangular when viewed end on. The two radially outwardly extending portions 302 and 304 are generally centered around a pear shaped portion 310.

Figure 28:
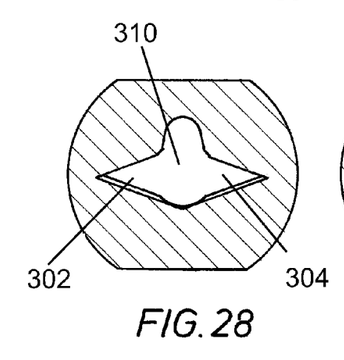
FIG. 28 is a cross-sectional view taken along the line 28-28 of FIG. 27.
Figures 29, 30:
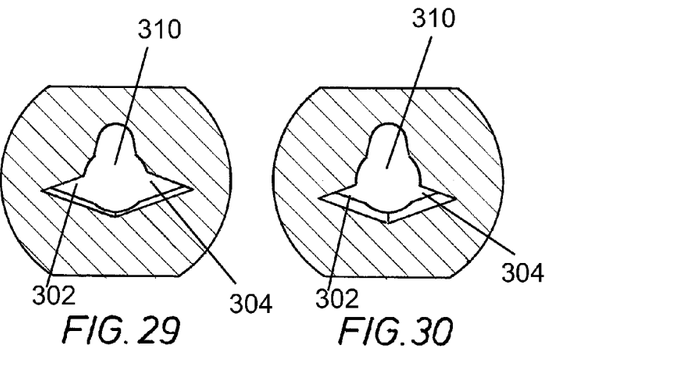
FIG. 29 is a cross-sectional view taken along the line 29-29 of FIG. 27.
FIG. 30 is a cross-sectional view taken along the line 30-30 of FIG. 27.

As shown in FIG. 27, radially extending portions 302 and 304, and pear shaped portion 310 all extend generally longitudinally into body 210 of driver 200. Body 210 has a generally centrally located imaginary axis C which extends through the pear shaped portion 310 of receiving formation 220. Pear shaped portion 310 maintains its orientation in relation to axis C along the entire length of receiving formation 220. Radially extending portions 302 and 304, however, extend generally longitudinally into receiving formation 220 at an angle relative to axis C. Thus, as demonstrated by FIGS. 28-30, when viewed in transverse cross-section pear shaped portion 310 is in the maintains the same shape and location throughout the length of receiving formation 220. However, the transverse cross-sections of radially extending portions 302 and 304 change as a result of being angled throughout the length of receiving formation 220. Specifically, FIG. 28 shows a tranverse cross-section of radially extending portions 302 and 304 and pear shaped portion 310. In FIG. 28, the greater part of the cross-section of pear shaped portion 310 is encompassed within the cross-sections of radially extending portions 302 and 304. In FIG. 29, radially extending portions 302 and 304 are further offset from axis C than in FIG. 28, while pear shaped portion 310 maintains the same shape and remains in the same orientation to axis C as shown in FIG. 26 and FIG. 28. FIG. 30 shows an even greater angular offset of radially extending portions 302 and 304 from axis C, while pear shaped portion 310 again maintains its same shape and orientation relative to axis C.

Again, it will be understood that while a preferred embodiment is depicted in the figures, the exact shape of receiving formation 220 can vary to fit the dimensions of the specific implant to be driven.

Figure 22:
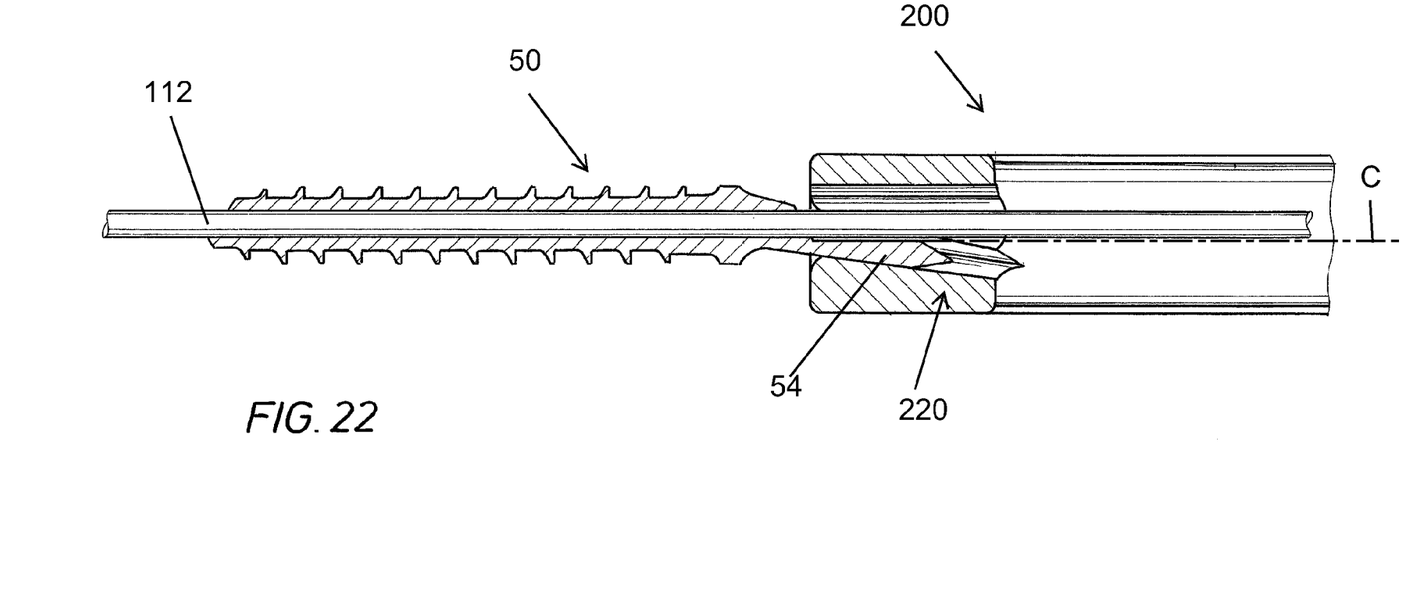
FIG. 22 is a cross-sectional view taken along the line 22-22 of FIG. 21.
Figure 23:
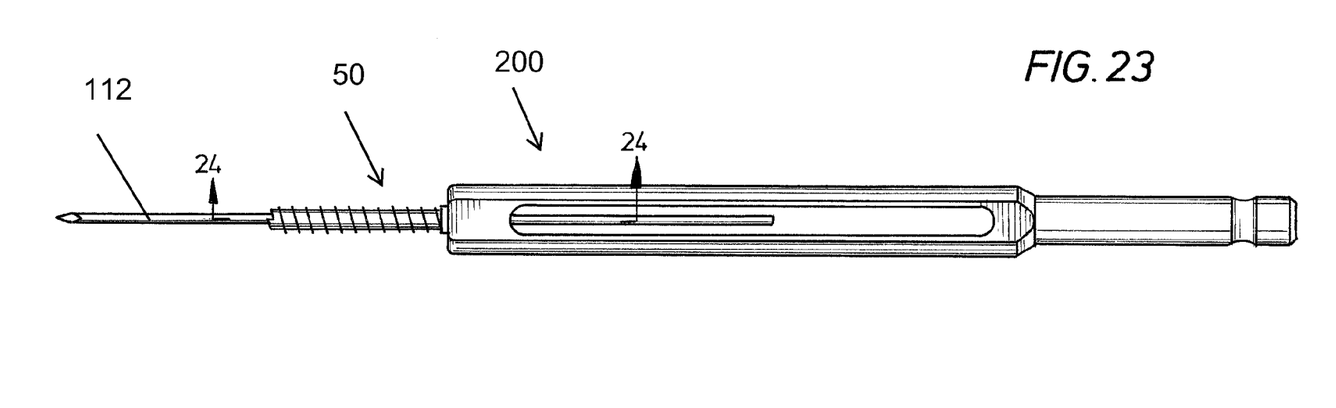
FIG. 23 is a top view of the driver of the present invention when the implant of the present invention is fully inserted into the driver.
Figure 24:
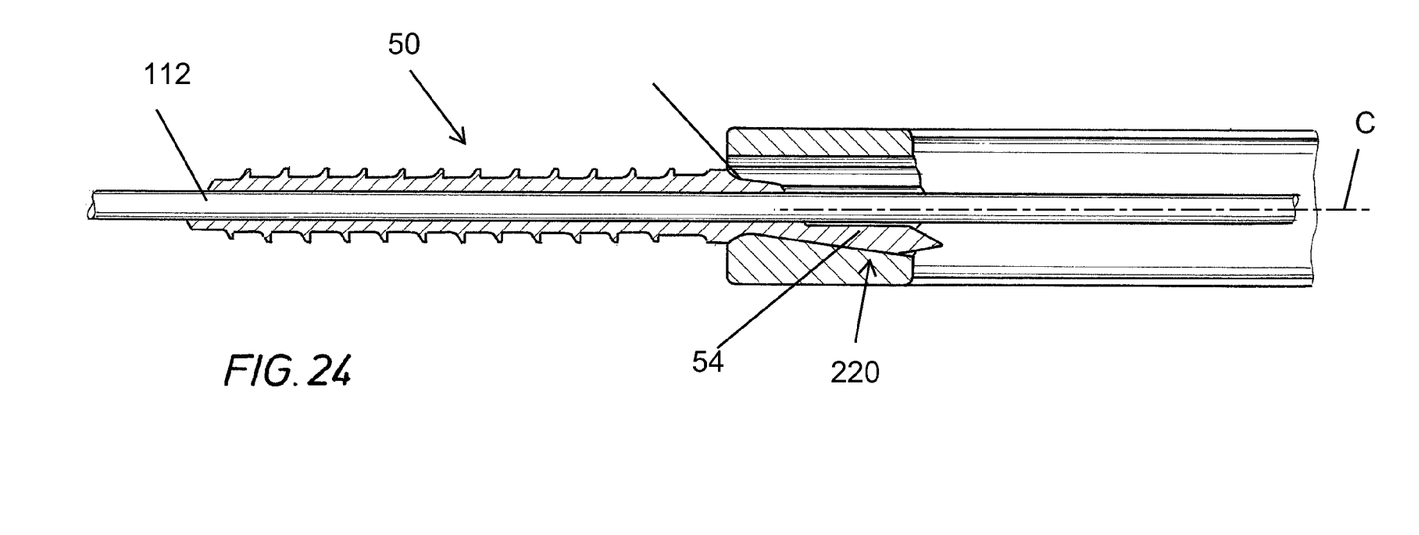
FIG. 24 is a cross-sectional view taken along the line 24-24 of FIG. 23.

Returning now to FIGS. 18-22 there is shown a progression of driver 200 engaging implant 50, threaded on K-wire 112. As discussed above, with reference to FIGS. 1-6, a K-wire 112 is introduced through a resected surface of the proximal phalanx, an implant is slid over the K-wire, the K-wire extending through the cannula, and a driver engages the head of the implant and threads the implant into the resected surface of the phalanx. As shown in FIG. 18, K-wire 112 extends through cannula 62 of implant 50 and into receiving formation 220 of driver 200. FIGS. 20, 22, and 24, show close up and in cross-section, how head 54 interfaces with receiving formation 220 as driver 200 engages implant 50. As shown in FIG. 20, as driver 200 approaches implant 50, but before driver 200 engages implant 50, head 54 of implant 50 is generally aligned with a central axis C running the length of driver 200, while K-wire 112 is offset from axis C. In FIG. 22, as driver 200 begins to engage implant 50, head portion 54 follows the path of the radially extending portions 302 and 304 along receiving formation 220, while K-wire 112 follows the path of pear shaped portion 310 along receiving formation 220. Thus, head portion 54 is angled away from central axis C, while K-wire 112 is brought closer to central axis C. As seen in FIG. 24, when implant 50 is fully engaged by receiving formation 220, and thus by driver 200, K-wire 112 is in alignment with central axis C of driver 200.

After engagement of implant 50 by driver 200, driver 200 can then be rotated about its central axis, in order to drive shank 52 of implant 50 into the resected phalanx. The alignment of the K-wire along central axis C of driver 200 ensures shank 52 of implant 50 will not be driven in at an offset or angle, but rather will be inserted straight into the bone. Without such alignment, during the driving of shank 52, K-wire 112 would be rotated off-center resulting in what is generally known as a "helicopter" movement. To prevent the helicopter movement of K-wire 112, it is important that the alignment of K-wire 112 remain centralized along the length of implant 50 and of driver 200.

In a preferred embodiment, body 210 of driver 200 has a central bore 260 for receiving K-wire 112. In a more preferred embodiment, body 210 also has first and second sides 212 and 214 positioned radially opposite one another, each of first and second sides 212 and 214 having elongate windows or openings 213 and 215, respectively, extending to said central bore 260. The wide central bore 260 with radially opposite windows 213 and 215 provides a manufacturing advantage in making the drivers of the present invention. Typical drivers in the prior art are solid cylinders with a bore driven longitudinally through to accept the K-wire as the implant is driven in. The act of machining such a long bore at such a small scale is difficult and often results in the bore being slightly offset. This can also result in the undesirable "helicopter" movement of the K-wire as the implant is driven into the bone by the driver. In the present invention, body 210 of driver 200 is generally open with windows extending to a central bore. Thus, the need to drill a narrow bore along the length of the body of the driver is eliminated. After passing through receiving formation 220, the K-wire is in a generally open area or bore 260 between windows 213 and 215. This design provides a distinct advantage in manufacturing the driver as well as ensuring the centralized alignment of the K-wire during the implant driving process.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A surgical implant, comprising:
   a threaded shank;
   a head, said head comprising a body portion proximate said shank and a nose portion distal said shank, said body portion having at least two laterally outwardly projecting fins, each of said fins comprising a plurality of axially spaced serrations, at least some of said serrations being tapered in two dimensions such that they terminate at their laterally outermost ends at substantial single discrete points; and
   a cannula extending through said shank and said head, said cannula adapted to receive a K-wire whereby said implant can be used to conduct interphalangeal surgery.

2. The surgical implant of claim 1, wherein said cannula is straight.

3. The surgical implant of claim 1, wherein said head is angled relative to a longitudinal axis extending through said shank.

4. The surgical implant of claim 3, wherein said cannula is straight.

5. The surgical implant of claim 1, wherein said body portion is widest proximate said shank and narrowest proximate said nose portion.

6. The surgical implant of claim 1, wherein said body portion is generally oblong shaped when viewed in transverse cross-section.

7. The surgical implant of claim 6, wherein said body portion is generally diamond-shaped when viewed in transverse cross-section.

8. The surgical implant of claim 1, wherein at least one of said serrations has an included angle of less than 90°.

9. The surgical implant of claim 1, wherein said nose portion is generally wedge shaped.

10. The surgical implant of claim 1, wherein each of said serrations terminate at their laterally outermost ends at a single discrete point.

11. A surgical implant, comprising:
    a threaded shank;
    a head, said head comprising a body portion proximate said shank and a nose portion distal said shank, said body portion having at least two laterally outwardly projecting fins, each of said fins comprising a plurality of axially spaced serrations, at least some of said serrations being tapered in two dimensions such that they terminate at their laterally outermost ends at substantial single discrete points, said head being angled relative to a longitudinal axis extending through said shank; and
    a straight cannula extending through said shank and said head, said straight cannula adapted to receive a K-wire whereby said implant can be used to conduct interphalangeal surgery.

12. The surgical implant of claim 11, wherein said body portion is widest proximate said shank and narrowest proximate said nose portion.

13. The surgical implant of claim 11, wherein said body portion is generally oblong shaped when viewed in transverse cross-section.

14. The surgical implant of claim 13, wherein said body portion is generally diamond-shaped when viewed in transverse cross-section.

15. The surgical implant of claim 11, wherein at least one of said serrations has an included angle of less than 90°.

16. The surgical implant of claim 11, wherein said nose portion is generally wedge shaped.

17. The surgical implant of claim 11, wherein each of said serrations terminate at their laterally outermost ends at a single discrete point.

18. A system for implanting a surgical implant, said system comprising:
    an implant, said implant comprising:
      a threaded shank;
      a head, said head comprising a body portion proximate said shank and a nose portion distal said shank, said body portion having at least two laterally outwardly projecting fins, each of said fins comprising a plurality of axially spaced serrations, at least some of said serrations being tapered in two dimensions such that they terminate at their laterally outermost ends at substantial single discrete points, said head being angled relative to a longitudinal axis extending through said shank;

a straight cannula extending through said shank and said head and said head, said straight cannula adapted to receive a K-wire whereby said implant can be used to conduct interphalangeal surgery;

a driver for driving said implant, said driver comprising:

a body having a first end, a second end, a longitudinally extending, generally central axis, and an opening in open communication with a receiving formation formed in and extending generally longitudinally into said body, said receiving formation having at least two radially outwardly extending portions offset from said central axis of said body and a pear shaped portion along said central axis of said body; and a K-wire, said K-wire extending through said cannula and into said driver.

19. The system of claim 18, wherein said radially outwardly extending portions of said driver are generally triangular when viewed in cross-section.

20. The system of claim 18, wherein said radially outwardly extending portions of said driver extend longitudinally along said receiving formation at an angle relative to said central axis of said body.

21. The system of claim 18, wherein said receiving formation of said driver is in open communication with a central bore extending longitudinally through a portion of said body.

22. The system of claim 21, wherein said body of said driver has a first side and a second side opposite said first side, said first and second sides each having elongate windows in open communication with said central bore.

* * * * *